United States Patent [19]

Kenny et al.

[11] Patent Number: 5,042,501
[45] Date of Patent: Aug. 27, 1991

[54] APPARATUS AND METHOD FOR ANALYSIS OF EXPIRED BREATH

[75] Inventors: Donald V. Kenny, Columbus; Thomas J. Kelly, Worthington, both of Ohio

[73] Assignee: Battelle Memorial Institute, Columbus, Ohio

[21] Appl. No.: 518,010

[22] Filed: May 1, 1990

[51] Int. Cl.$^5$ ............................................. A61B 5/097
[52] U.S. Cl. .................................................. 128/719
[58] Field of Search ................ 128/716, 719, 725, 730

[56] References Cited

U.S. PATENT DOCUMENTS 4,485,822 12/1984 O'Conner et al. .................. 128/719
4,850,371 7/1989 Broadhurst et al. ................. 128/719

FOREIGN PATENT DOCUMENTS 0153741 9/1985 European Pat. Off. ............ 128/719

Primary Examiner—William E. Kamm
Assistant Examiner—Scott R. Akers
Attorney, Agent, or Firm—Klaus H. Wiesmann

[57] ABSTRACT

Apparatus and method for providing breath for introduction to a measuring device such as a mass spectrometer. The apparatus includes a mouthpiece for interfacing a subject with the apparatus; a tube for carrying exhaled breath from the subject to the inlet of a mixing chamber; a mixing chamber having an inlet, sample outlet and exit tube, that provides a residence time for the exhaled breath sufficient to mix the breath and provide an adequate sample to the measuring device; and heating apparatus for maintaining the apparatus above a temperature where condensation of vapor occurs.

18 Claims, 4 Drawing Sheets

APPARATUS AND METHOD FOR ANALYSIS OF EXPIRED BREATH

FIELD OF THE INVENTION

The invention serves as an interface between a subject (human or animal) and a measuring device. The invention differs from prior art in that whole (i.e. undiluted) breath is analyzed in a realtime continuous manner. No preanalysis collection or concentration is needed, and rapid response is achieved. No subject intervention is needed to control the introduction of breath except to breathe normally. In one embodiment of the invention for analysis of human breath, a 3 liter mixing chamber is continuously purged by breath; by sampling from this chamber at a constant flow rate a continuous realtime analysis of breath can be performed for clinical toxicology, occupational medicine and exercise physiology studies.

BACKGROUND OF THE INVENTION

The assessment of individual personal exposure to toxic substances is an important component of human and animal health risk assessment. Assessment of exposure by the analysis of breath is particularly attractive since it is noninvasive and nontraumatic for the subject. Breath may also be a less complex medium than blood or urine, and so may be easier to analyze and characterize. For these reasons, breath analysis has been applied in several studies addressing exposure to toxic chemicals, or investigating natural metabolites such as indicators of disease, see for example: A. Zlatkis, R. Brazell, and C. Poole, *Clin. Chem.*, 27, 289-297, 1981; B. Krotoszyinski, G. Gabriel, and H. J. O'Neill, *Chrom. Sci.*, 15, 239, 1977; S. Chen, L. Zieve, and V. Mahadevan, *J. Lab. Clin. Med.*, 75, 628-635, 1970; M. Simenhoff, J. Burke, J. Saukkonen, A Ordinavio, and R. Doty, *New England J. Med.*, 297, 132-135, 1977; B. Lorber, *Amer. Rev. Resp. Dis.*, 112, 875-877, 1975; F. Brugnone, L. Perbellini, P. Apostoli, and E. Gaffuri, "Monitoring of Industrial Exposure to Organic Volatile Compounds by Analysis of Alveolar Air and Blood", American Chemical Society 187th National Meeting, St. Louis, Mo., 1985; M. Hisamura, *Nippon Naika Gakkai Zasshi*, 68, 1284-1292, 1979; A. Tangerman, M. T. Meuwese-Arends, J. H. M. van Tongeren, *J. Lab Clin. Med.*, 106, 175-182, 1985; L. Campbell, D. M. Marsh, and H. K. Wilson, *Ann Occup. Hyg.*, 31, 121-133, 1987; R. W. Handy, H. L. Crist, T. W. Stanley, "Quality Assurance For Personal Exposure Monitoring", in *Quality Assurance For Environmental Measurements*, ASTM Special Technical Publication No. 867, 284-296, 1985; and A. W. Jones, G. Maardh, E. Aenggard, *Pharmoacol. Biochem. Behav.*, 18, 267-272, 1983. In most of the studies breath analysis has been performed by integrated collection of breath in bags, on sorbent materials, or in cryogenic traps. Such approaches may suffer from poor time resolution, inefficient sample collection or recovery, or sample degradation.

Further, breath analysis is useful in the study of natural metabolites, including indicators of disease, as well as bodily effects due to exposure to toxic chemicals. By monitoring whole breath continuously, in realtime, many studies in chemical toxicology, occupational medicine and exercise physiology can be performed.

Recently attempts have been made to apply the considerable sensitivity and selectivity of tandem mass spectrometry (MS/MS) to breath analysis, by employing atmospheric pressure chemical ionization (APCI) as the ionization source, see for example: A. M. Lovett, N. M. Reid, J. A. Buckley, J. B. French, and D. M. Cameron, *Biomed. Mass Spectrom.*, 6, 91-97, 1979 F. M. Benoit, W. R. Davidson, A. M Lovett, S. Nacson, and A. Ngo, *Anal. Chem.*, 55, 805-807, 1983; and F. M. Benoit, W. R. Davidson, A. M. Lovett, S. Nacson, and A. Ngo, *Int. Arch. Occup. Environ. Health*, 55, 113-120, 1985. However, such efforts have been limited by the means used to introduce breath into the mass spectrometer. The breath inlets used required the subject to control his breath flow rate or an observed pressure gauge reading during exhalation, required dilution of breath with a continuous flow of clean air, and provided only intermittent data (i.e., during each exhalation).

Other relevant art known to the inventors includes the following U.S. Pat. No.: 4,772,559 to Preti et al. discloses a method of detecting and diagnosing an individual to determine the presence of bronchiotic carcinoma by analysis of expired lung air; U.S. Pat. No. 4,485,822 to O'Connor et al. relates to a system and method for interfacing a patient with equipment for monitoring gaseous components of the exhalation of the patient and emphasizes the elimination of dead space volume and a disc filter for removing secretions and humidification; U.S. Pat. No. 4,178,919 to Hall reveals a flowmeter for providing synchronized flow data and respiratory gas samples to a medical mass spectrometer; U.S. Pat. No. 4,167,667 to Fletcher, et al. discloses a respiratory gas moisture separator system for mass spectrometer monitoring systems that relies on a pressure drop to maintain moisture in the vapor state and a momentum separator to remove water droplets; U.S. Pat. No. 3,759,249 to Fletcher, et al. relates to a method and apparatus for obtaining an analysis of respiratory gas flow rate and frequency of inspiration and expiration cycles on a "real time" basis; U.S. Pat. No. 3,649,199 to Littlejohn reveals a method for detecting trace quantities of an organic drug material in a living animal and relies on a membrane gas separator for direct breath analysis (column 3, lines 29-32); U.S. Pat. No. 3,622,278 to Etzinga discloses a method and means for measuring and analyzing the composition of alveolar air for determining the volatile constituents in blood. The device eliminates air from the dead air spaces of the respiratory tract thereby avoiding dilution of alveolar air.

An object of the present invention is to provide an improved breath interface which allows continuous analysis of undiluted breath by APCI/MS/MS. A further object is to provide an improved breath interface that reduces the loss of trace constituents in breath to a minimum. A still further object is to provide an improved breath interface that is easy to use and reliable.

BRIEF DESCRIPTION OF THE INVENTION

A breath interface apparatus provides breath for introduction to a measuring device. It consists of subject interface means for interfacing the subject with the apparatus; tube means for carrying exhaled breath from the subject interface means to the inlet of a mixing chamber; a mixing chamber having an inlet, sample outlet and exit tube means, that provides a residence time for the exhaled breath sufficient to mix the breath and provide a sufficient sample to the measuring device; and heating means for maintaining the apparatus above a temperature where condensation of vapor occurs.

A method for measuring trace constituents in a subject's breath encompasses providing a subject interface means to obtain breath from the subject; flowing breath obtained from the subject to a mixing chamber; mixing the breath in the mixing chamber; flowing breath samples from the mixing chamber to a measuring device and exiting unneeded breath from the mixing chamber; and maintaining the breath above the condensation temperature of vapor in the breath and preventing condensation on the apparatus by heating.

DETAILED DESCRIPTION OF THE INVENTION

In general, the apparatus of the invention functions as an interface between a subject and a measuring device. In a preferred embodiment of the invention the apparatus acts as an interface between a subject and a mass spectrometer.

Figure 1:
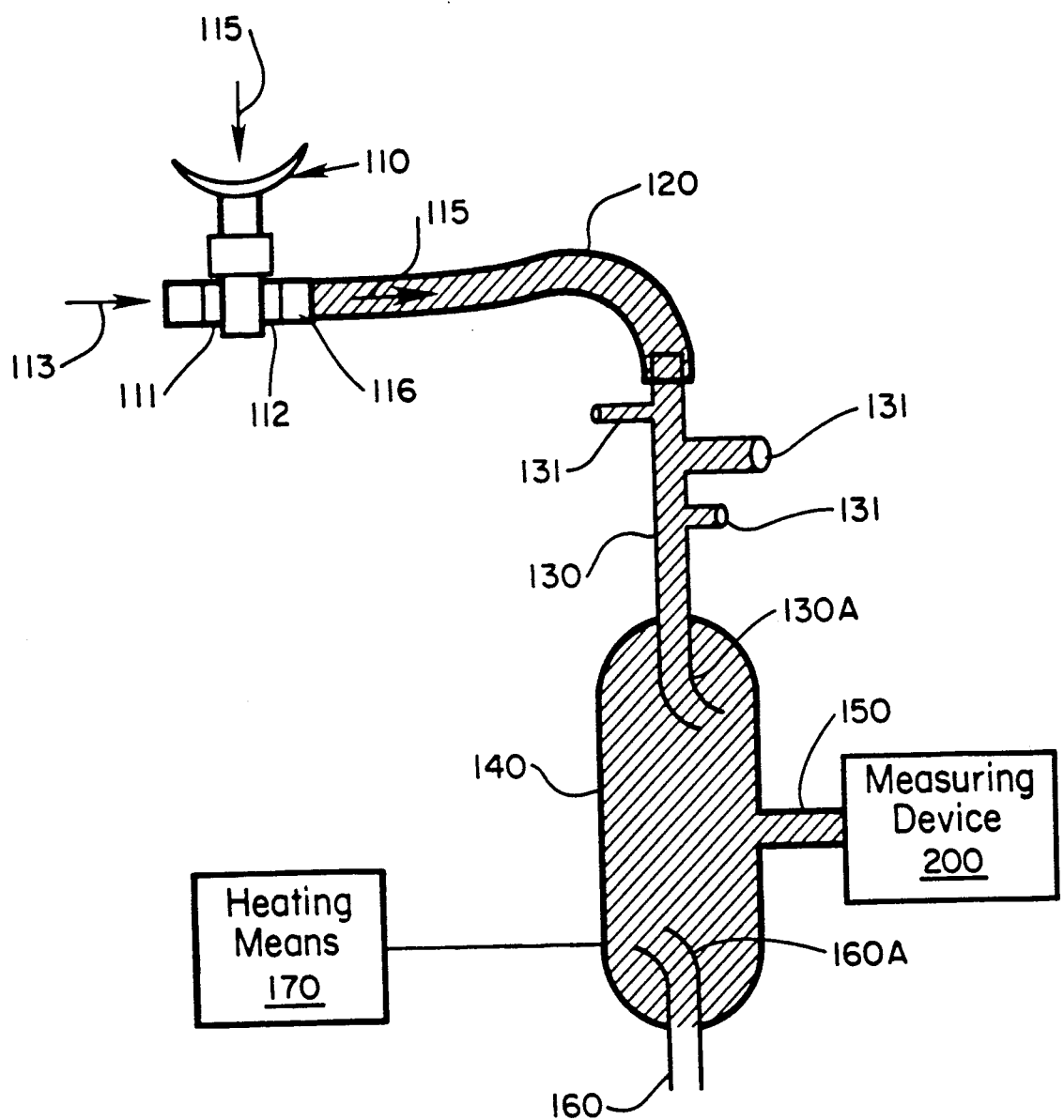
FIG. 1 is a semischematic drawing illustrating details of the apparatus of the invention.

The breath interface 100 is shown in FIG. 1 for providing exhaled breath. A subject uses a conventional mouthpiece 110 (subject interface means) and breathes normally. One way breathing valves 111,112 (e.g. Hans Rudolph Model 2600) are arranged in relation to the mouthpiece 110 so that exhaled breath 115 is pushed into the inlet 116 while inhaled air 113 can be drawn from the room, from sources of clean air, or from prepared gas mixtures (not shown). By this means, the air supplied to the subject can be controlled without hindering the exhalation mechanism. Alternatively, other apparatus (having the function of a mouthpiece e.g. tracheotomy tube) known in the art for interfacing with a subject may be used to obtain a breath sample 115 from the subject. The breath sample 115 is then transported through a large diameter tube 120 (preferably flexible and of Teflon), to inlet tube 130 and past gas inlet ports 131, and into a mixing chamber 140. The entire flow system from the mouthpiece 110 to the measuring device 200 is heated by heating means 170 to prevent condensation of exhaled water vapor and minimize surface losses of trace substances in the breath sample. The heated portion is depicted by the shaded area in FIGS. 1 and 3. If desired, the mouthpiece (subject interface means) 110 may also be heated. The gas inlet ports 131 may be used to flush the system with zero air, add gaseous standards, or allow the withdrawal of sample for other tests. The breath sample is drawn into the measurement device 200 through sample outlet tube 150. Excess exhaled air 115 is vented at a large bore exit tube 160. Inlet tube 130 and exit tube 160 preferably extend into the mixing chamber 140 and preferably have bent portions 130A,160A respectively that are oriented in opposite directions to promote mixing of the continuous breath sample. Alternatively, baffles (not shown) could be used at the inlet and exit tubes 130,160 as is known in the art to promote mixing. Mixing chamber 140 may be of glass, stainless steel, nickel, Teflon or similar material or other materials lined with these. Connectors and adaptors may be of similar materials. If desired the mixing chamber may be of flexible materials or have movable walls (not shown) to allow adjustment in volume.

The size of the mixing chamber can be adjusted to obtain a residence time of about 1 to 60 seconds. At high breath rates the residence time can be very short whereas at low rates longer residence times are required to achieve an integrated sample. Flow rates and size of the mixing chamber are related to the breath rate provided by the subject. For example, if the subject tested is a small animal having a low breath rate (e.g. dog, cat, mouse) the mixing chamber and flow rate are scaled down to provide proper residence times and sample flow rates. Sample flow to the TAGA must be adjusted to be lower than the lowest flow of breath from the subject to preserve sample integrity. Exhaust vacuum at sample outlet 212 can be adjusted to accommodate high or low flow rates. Flow rates may be as low as about 0.1 liters/minute and as high as about 100 liters/minute.

Heating means 170 uses preferably resistance wire heating and associated control means where the heating wires are wound around or placed over the surfaces to be heated. Additionally, insulation (not shown) may be used in conjunction with heating means 170 if needed or desired for better control. It is the use of heating means 170 that provides the desired reduction in the loss of trace constituents of sampled breath by preventing condensation of vapor.

Exhaled breath is normally saturated with water vapor (100 per cent relative humidity). The exhaled breath is also normally at or very near body temperature. For humans this temperature is about 37 C. (98.6 F.), but will vary for each subject. Thus, the heating means must maintain all parts of the apparatus in contact with expired breath above the temperature where condensation would occur. These temperature relationships can easily be determined by those skilled in the art. It is preferred that a temperature slightly higher than the subjects body temperature be used.

The prevention of condensation is important since any condensate will remove trace components from the sampled breath and give false readings. Of similar importance is the need to provide materials or lining for the tubing, connectors, mixing chamber, etc. that will not absorb, adsorb or otherwise react with breath components.

Figure 2:
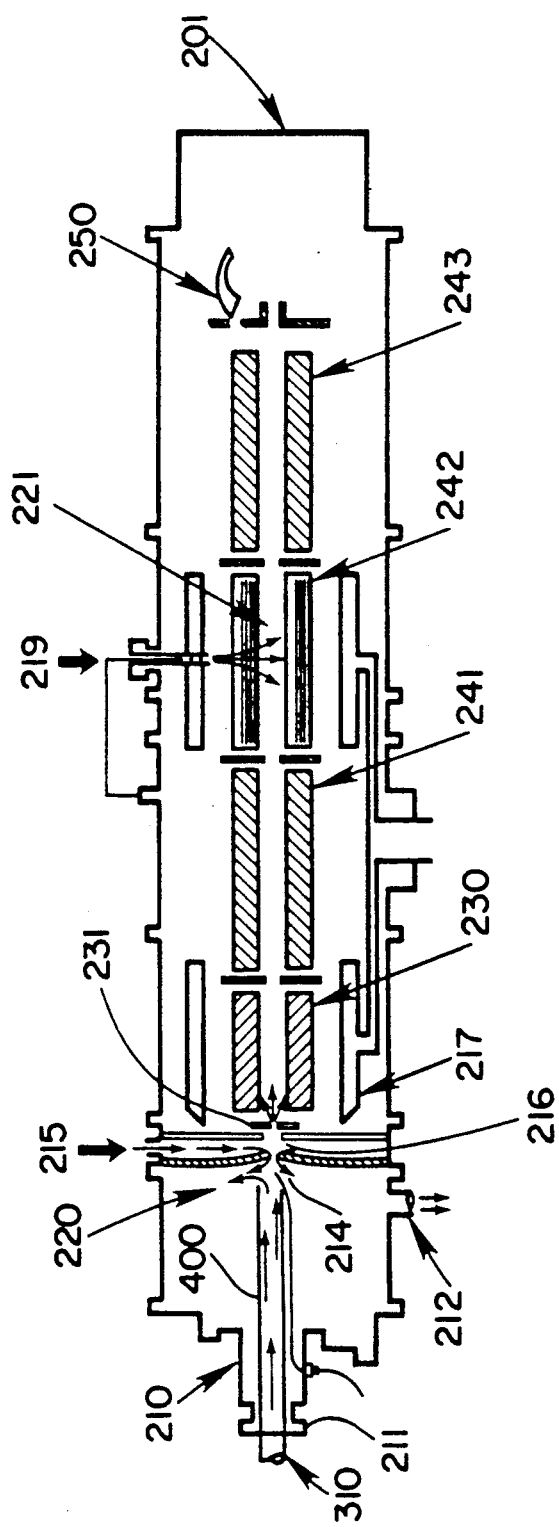
FIG. 2 is a semischematic drawing depicting exemplary components of a TAGA (Registered Trademark) instrument useful with the invention.

The measuring device 200 used in the examples below was a TAGA mass spectrometer 201 (Model 6000E), an atmospheric pressure chemical ionization (APCI) tandem mass spectrometer. It is a sensitive, specific, fast, and versatile analyzer for air analysis. Components of the TAGA 201 are illustrated in FIG. 2. The basic components are the inlet module 210, ionization source 220, transfer ion lenses 230, three quadruple mass filters 241, 242, 243, and the detector 250. Samples of air streams are introduced at sample inlet 211 and exhausted at sample exhaust 212. Trace contaminants in the sampled air stream are ionized by a corona discharge 214 at atmospheric pressure. Ionized molecules are electrically accelerated through a counter current flow of dry nitrogen 215 toward a small orifice 216 where they are carried into a cryogenic vacuum system 217 by a small flow of nitrogen gas. The ion transfer lenses 231 eliminate the majority of the nitrogen gas while electrically focusing the ions into the first quadruple mass analyzer 241. The first quadruple 241 typically functions as a mass filter by eliminating all but those ions of a specific mass of interest. The mass of interest is selected to correspond to a molecular ion of a particular contaminant which may also include molecular or fragment ions of interfering species. Ions passing through the first quadruple 241 are accelerated into the second quadruple 242 where they are intercepted by a neutral beam of argon 219 or other inert gas atoms. Collision with argon atoms at region 221 results in fragmentation of the ions in a predictable manner characteristic of their molecular structure. Fragments resulting from the molecular ion of interest are then sorted out from fragments of interfering ions by the third quadruple 243 mass analyzer. As a result of the tandem mass analyzers, the TAGA achieves a highly specific measurement for a given combination of mass analyzer settings. The TAGA can monitor several specific target compounds simultaneously or can scan a mass range for compounds which have a common structural feature. Conventional scanning modes provide information for the identification of unknowns.

When a TAGA spectrometer 201 is used for example with a human subject, samples are removed from the mixing chamber 140 by way of outlet tube 150 at a constant flow of about 3 L/min. This is greatly reduced from the typical TAGA flow of 30-100 L/min used in atmospheric sampling.

Figure 3:
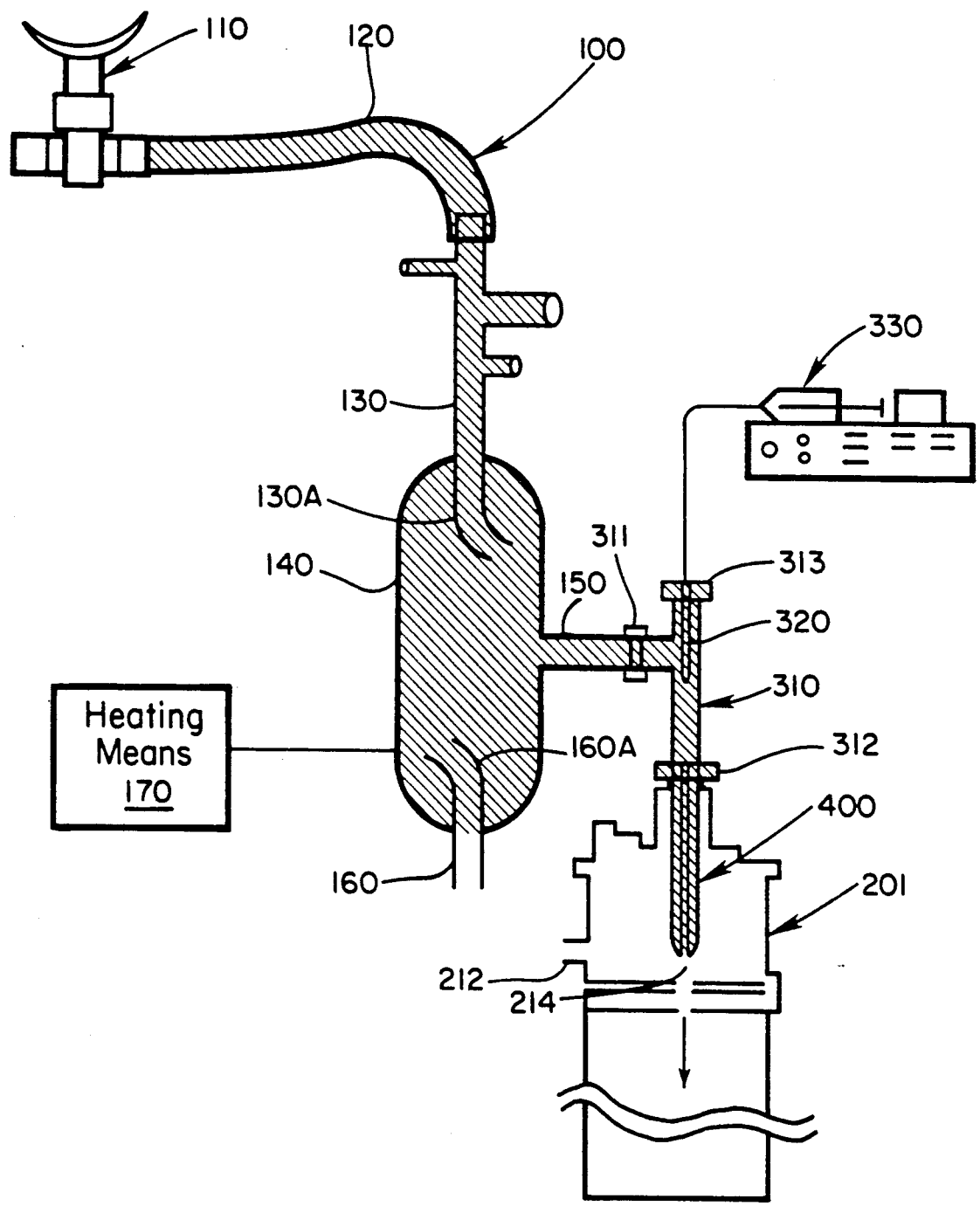
FIG. 3 is a semischematic drawing illustrating details of the apparatus when used with a TAGA instrument as the measuring device.

Referring to FIG. 3, an adaptor 310 provides for connection to outlet tube 150, the sample inlet tube 400 to the TAGA, and vaporizer probe 320 with unions 311, 312 and cap 313. The original sample inlet tube to the TAGA is replaced by a narrow bore sample inlet tube 400 which enhances sensitivity in breath analysis by more efficiently directing sample flow into the ionization region 214. The liquid vaporizer probe 320 is supplied by an external calibration source, a syringe drive 330 is depicted, that delivers calibration solutions into the TAGA sample flow that flows from tube 150 through connector 310 to sample inlet tube 400, allowing standard additions to the breath sample without interrupting analysis. In the examples herein aqueous lactic acid solutions of $10^{-4}$M were used for calibration. A human adult subject even at rest can easily supply more than the 3 L/min flow required by the TAGA as configured in the preferred embodiment for human subjects as described herein; the large bore exit tube 160 allows excess breath to be diverted with negligible flow restriction. This exit tube 160 can also be used to supply breath for other tests.

The apparatus and method may be adapted to other mass spectrometers by controlling the flow of sample gases. For example, with the TAGA it does not matter if water vapor is in the sample. With other mass spectrometers this may be a problem and the water vapor will have to be removed. This will not work as well since trace species will be removed with the water.

Figure 4:
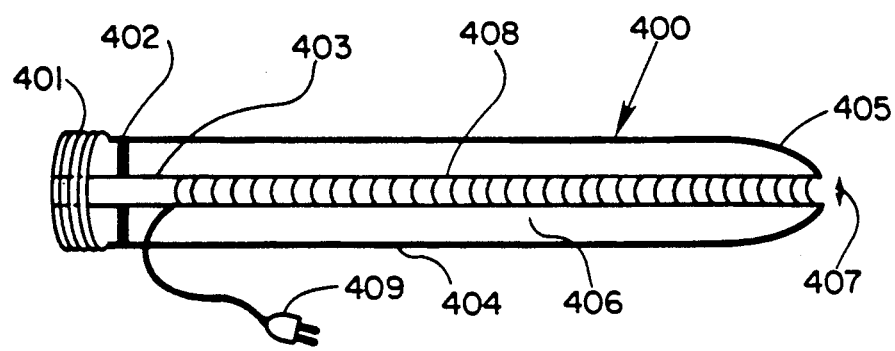
FIG. 4 is a drawing of details of a narrow bore inlet tube that is preferred when using the apparatus with a TAGA instrument.

FIG. 4 provides details of the inlet tube 400. The inlet tube 400 is secured to the system by a threaded connection 401 that provides support and seals the TAGA 201 and adaptor 310 with union 312. The inlet tube comprises an inner tube 403 and outer tube 404. The inner tube 403 is sealed at one end 405 to outer tube 404 while Teflon ring 402 provides for support between tubes 403, 404 at their other ends and seals the space 406 between them. The diameter of the bore 407 in tube 403 is reduced to 6 mm from that of the inlet tube normally used in the TAGA 201. This reduction in the tube size provides improved transport of the breath flow into the ionizing region 214 of the TAGA 201, resulting in a sensitivity about five (5) times higher than that obtained with the larger tube. Nonionized sample then exits the TAGA through outlet 212 to a pump (not shown). Ions from the sample proceed to detection as described above. The inner tube 403 is heated by heating tape or similar auxiliary heating means 408 that is connected to heating means 170 by connector 409.

The diameter of bore 407 may be further adjusted to accommodate lower flows other than those used with the human subjects described herein. Small mammals, for example, would require much smaller bores to improve sensitivity by improved transfer of sample into the ionization region 214. These can easily be determined by those skilled in the art having read the teachings herein.

The breath interface 100 has undergone a variety of tests. Heating of the breath flow path prevents condensation of breath moisture at breath flow rates from 5 to over 100 L/min, characteristic of subject activity levels ranging from rest to vigorous exertion. Calibrations have been performed using several different procedures in addition to the normal mode of calibration described above. The additional calibration tests have shown the same results when the calibration probe is positioned upstream of the breath interface 100 as when it is positioned in the normal downstream position (see FIG. 3). These tests have also shown no effect of flow rate in the breath interface 100 on TAGA response. Further tests using humidified air have disclosed no transient effects due to the introduction of humidity into the inlet, as occurs at the onset of breathing into the device. However, these tests and calibration procedures have shown that TAGA sensitivity to lactic acid in breath or in air with 100 percent humidity is reduced by about 30 percent relative to that in dry air. This finding indicates the need to calibrate by standard addition to the breath matrix, a capability which is built into the apparatus described herein.

Figure 5:
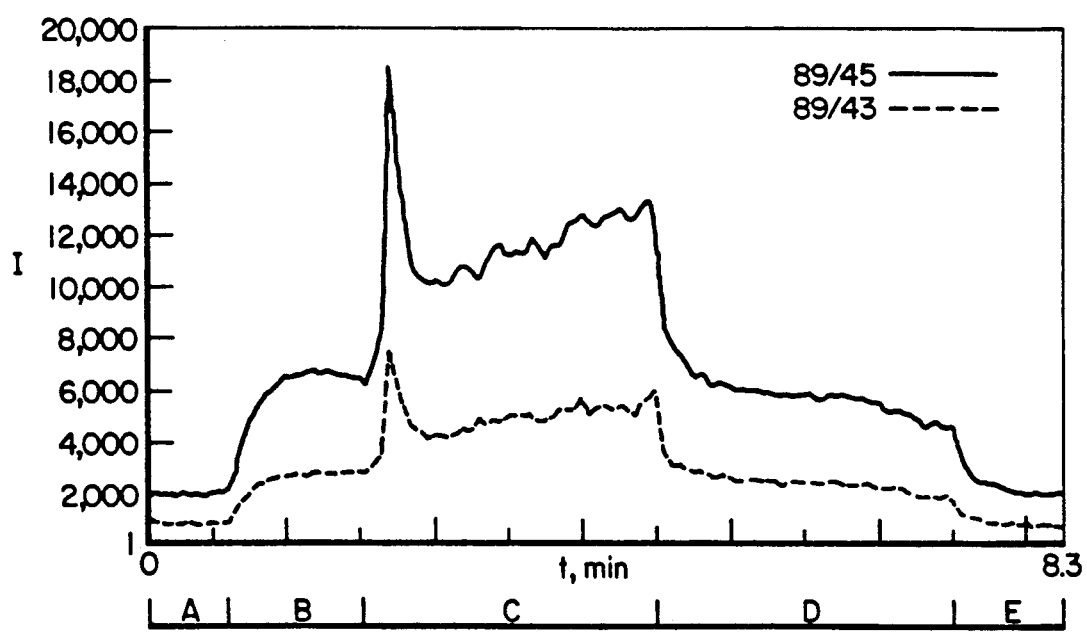
FIG. 5 is a graph illustrating the response of a TAGA spectrometer to lactic acid in breath and from a control when used with the apparatus of the invention.

As an example for detection of trace substances in breath, lactic acid has been monitored continuously in breath over time periods from a few minutes up to nearly an hour, during exercising of a human subject on a stationary bicycle. FIG. 5 shows an example of monitoring lactate in breath during a brief exercise period (time (t) in minutes on the x axis and intensity (I) in ion counts per second on the y axis). Lactic acid is detected by monitoring of daughter ions of masses 45 (solid line) and 43 (dotted line) arising from the fragmentation of lactate anion (mass 89). The graph shows the following periods as noted at the bottom thereof:

A. background, zero air
B. subject started breathing into inlet
C. 8.2 ppb standard addition with syringe drive introduction of lactic acid
D. subjects breath only, syringe drive off
E. zero air flush of system.

The subject began breathing into the mouthpiece 110 at rest, and after a short time began exercising on a stationary bicycle, continuing for several minutes until moderate exertion and resulting increased breath rate were reached. While the subject was exercising, lactic acid response was calibrated by standard addition to the breath flow. Then the subject stopped exercising, and finally the system was flushed with clean purified air. Response to the breath concentration of lactic acid was seen within five seconds once the subject started breathing into the system. An approximately steady state was quickly established with no evidence of variation of signal due to the breathing cycle.

Also of interest in FIG. 5 are data from the end of the experiment. Region E shows a sharp decline in signal when the system is flushed with clean air and breath analysis ends. The lactic acid signal in zero air drops rapidly to that seen before the breath analysis, indicating little memory effect in the breath interface 100.

A standard addition of lactic acid to the breath flow is superimposed upon the breath lactate signal in FIG. 5; the spike at the start of calibration is due to instability in the syringe drive/vaporizer system when first turned on. Lactate concentrations in breath shown in FIG. 5 and observed in other tests are a few ppbv, consistent with calculations based on the pKa and Henry's law constant for lactic acid, roughly millimolar concentrations of lactate in blood, and a pH for body fluids of about 7. Acetic and pyruvic acids were also monitored in some tests, and were present at concentrations well below those of lactic acid. The continuous and stable response shown in FIG. 5, which contrasts with the results of the prior art employing APCI/MS/MS in which measurements were made only on individual exhalations. The lactate concentration in whole breath was generally observed to remain constant or to decrease during the exercise tests as breathing rate increased. However, calculations incorporating breath flow rate indicate that the total output of lactate in breath increased greatly during exercise, parallel to the power output of the subject. The amounts of lactic acid excreted in breath are negligibly small compared to the total amount of lactic acid in other reservoirs within the body; however, these tests on breath lactate serve to illustrate the use of the device in breath analysis for industrial hygiene tests, hazardous material exposure studies, bioresponse tests, pharmaceutical kinetic studies, and disease detection. For example, workers in a chemical plant would be monitored for chemicals they were exposed to such as organic solvents (benzene, toluene and the like); human or animal subjects would be monitored to determine metabolism of foods (e.g. breath fresheners, artificial sweeteners); human or animal subjects would be monitored for the metabolism of drugs in the body versus time (e.g. anesthetics); subjects would be monitored for detection of compounds indicative of disease (e.g. sulfur compounds in liver disfunction), or to determine levels of various compounds such as ammonia or acetone indicative of various body states, and so on.

The breath interface 100 requires no attention from the subject, and thus is applicable to subject activity ranging from rest to extreme exercise for a great latitude in breathing rates. The apparatus is useful for the flow rates indicated above.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

We claim:

1. An apparatus for providing breath from a subject for introduction to a measuring device comprising:
    a. subject interface means for interfacing the subject with the apparatus;
    b. tube means for carrying exhaled breath from the subject interface means to the inlet of a mixing chamber;
    c. a mixing chamber having an inlet, sample outlet and exit tube means, that provides a residence time for the exhaled breath sufficient to mix the breath and provide a sufficient sample to the measuring device; and
    d. heating means for maintaining b. and c. above a temperature where condensation of vapor occurs.

2. The apparatus of claim 1 comprising:
    e. adaptor means for introducing sample breath from the mixing chamber to a measuring device; and
    f. additional heating means for maintaining the adaptor means above a temperature where condensation occurs.

3. The apparatus of claim 1 wherein the heating means includes means for maintaining the subject interface above the temperature where condensation of vapor occurs.

4. The apparatus of claim 1 wherein the subject interface means constitutes a mouthpiece or a tracheotomy tube.

5. The apparatus of claim 1 wherein the tube means has means for connection to a mass spectrometer.

6. The apparatus of claim 1 wherein the mixing chamber has movable walls for adjustment of volume.

7. The apparatus of claim 1 wherein the heating means constitutes a resistance wire and associated control means.

8. The apparatus of claim 1 wherein a calibration device is connected to the sample outlet to provide standards for the measuring device.

9. The apparatus of claim 1 wherein the materials that constitute the breath interface apparatus are inert to the materials to be tested.

10. A method for measuring trace components in a subject's breath comprising:
    a. providing a subject interface means to obtain breath from the subject;
    b. flowing breath obtained from the subject to a mixing chamber:
    c. mixing the breath in the mixing chamber;
    d. flowing breath samples from the mixing chamber to a measuring device and exiting unneeded breath from the mixing chamber; and
    e. maintaining the breath in steps a, b, c, and d above the condensation temperature of vapor in the breath.

11. The method of claim 10 whereby the residence time is maintained between about 1 second to about 60 seconds.

12. The method of claim 11 whereby the residence time is maintained above about 30 seconds.

13. The method of claim 10 whereby the providing step includes a mouthpiece or a tracheotomy tube as the subject interface.

14. The method of claim 10 whereby the sample flow rate is maintained between about 0.1 liters per minute to about 100 liters per minute.

15. The method of claim 14 whereby the sample flow rate is maintained above about 3 liters per minute.

16. The method of claim 10 comprising:
    f. providing a mass spectrometer as the measuring device.

17. The method of claim 10, whereby the system is flushed with clean air between analysis.

18. The method of claim 10 whereby a calibration standard is injected into the breath samples from the mixing chamber.

* * * * *